United States Patent
Perot

(10) Patent No.: US 8,905,975 B2
(45) Date of Patent: Dec. 9, 2014

(54) CONTAINER, DEVICE AND METHOD TO STORE AND EXPEL A PRODUCT

(75) Inventor: Frédéric Perot, Saint Paul de Varces (FR)

(73) Assignee: Becton Dickinson France S.A.S., Le Pont de Claix (FR)

(*) Notice: Subject to any disclaimer, the term of this patent is extended or adjusted under 35 U.S.C. 154(b) by 743 days.

(21) Appl. No.: 12/441,043

(22) PCT Filed: Sep. 12, 2007

(86) PCT No.: PCT/IB2007/003493
§ 371 (c)(1),
(2), (4) Date: Oct. 13, 2009

(87) PCT Pub. No.: WO2008/032216
PCT Pub. Date: Mar. 20, 2008

(65) Prior Publication Data
US 2010/0106085 A1    Apr. 29, 2010

(30) Foreign Application Priority Data
Sep. 13, 2006  (FR) .................................... 06 07996

(51) Int. Cl.
*A61M 5/00*    (2006.01)
(Continued)

(52) U.S. Cl.
CPC ........... *A61M 5/31591* (2013.01); *A61M 5/284* (2013.01); *A61M 5/3146* (2013.01);
(Continued)

(58) Field of Classification Search
CPC ............ A61M 5/3158; A61M 5/3156; A61M 5/31591; A61M 5/31525–5/31595; A61M 5/2448; A61M 5/284; A61M 5/31511; A61M 2005/31508

USPC .................... 604/110, 117, 82–92, 207–211, 604/165.01–164.04, 186, 187
See application file for complete search history.

(56) References Cited

U.S. PATENT DOCUMENTS 2,047,010 A * 7/1936 Dickinson .................... 604/157
4,444,335 A   4/1984 Wood et al.
(Continued)

FOREIGN PATENT DOCUMENTS

CH     279779 A    12/1951
DE   10110126 A1   9/2002
(Continued)

OTHER PUBLICATIONS

Barrelle et al; Machine Translation of FR 2881052 published on Jul. 28, 2006.*

(Continued)

*Primary Examiner* — Quynh-Nhu H Vu
*Assistant Examiner* — Jenna Zhang
(74) *Attorney, Agent, or Firm* — Hoffmann & Baron, LLP

(57) ABSTRACT

The present invention relates to a container comprising: a body; a pusher movable with respect to the body between an initial position and an end-of-use position; a locker located on the pusher and forming an abutment so as to be able to abut against the body between the initial position and the end-of-use position, wherein, the abutment abuts against the body to limit distal movement of the pusher relative to the body to a pusher locking position located between the initial position and the end-of-use position; a locking arrangement capable of, temporarily, locking the locker on the pusher so as to define a locker locking position of the locker on the pusher, the locker locking position establishing the position of the abutment relative to the pusher so as to set the pusher locking position; and, an unlocking arrangement designed so that, with triggering, the locking arrangement is released so as to allow the locker to be displaced relative to the pusher and for the pusher to be moved past the pusher locking position toward the end-of-use position.

34 Claims, 6 Drawing Sheets

(51) Int. Cl.
    *A61M 37/00* (2006.01)
    *A61M 5/28* (2006.01)
    *A61M 5/31* (2006.01)
    *A61M 5/315* (2006.01)

(52) U.S. Cl.
    CPC ............ *A61M 2005/31508* (2013.01); *A61M 2005/3132* (2013.01); *A61M 5/31555* (2013.01); *A61M 5/3158* (2013.01)
    USPC .......................... 604/208; 604/89; 604/187

(56) References Cited

U.S. PATENT DOCUMENTS

| | | | |
|---|---|---|---|
| 5,080,649 A * | 1/1992 | Vetter | 604/91 |
| 5,328,486 A | 7/1994 | Woodruff | |
| 5,385,558 A | 1/1995 | Cottone, Sr. et al. | |
| 5,531,708 A * | 7/1996 | Woodruff | 604/208 |
| 6,419,656 B1 * | 7/2002 | Vetter et al. | 604/90 |
| 2005/0131354 A1 * | 6/2005 | Tachikawa et al. | 604/187 |

FOREIGN PATENT DOCUMENTS

| | | |
|---|---|---|
| EP | 1459776 | 9/2004 |
| FR | 2881052 A1 * | 7/2006 |

OTHER PUBLICATIONS

Barrelle et al; Machine Translation of FR2881052A1 published on Jul. 28, 2006.*

* cited by examiner

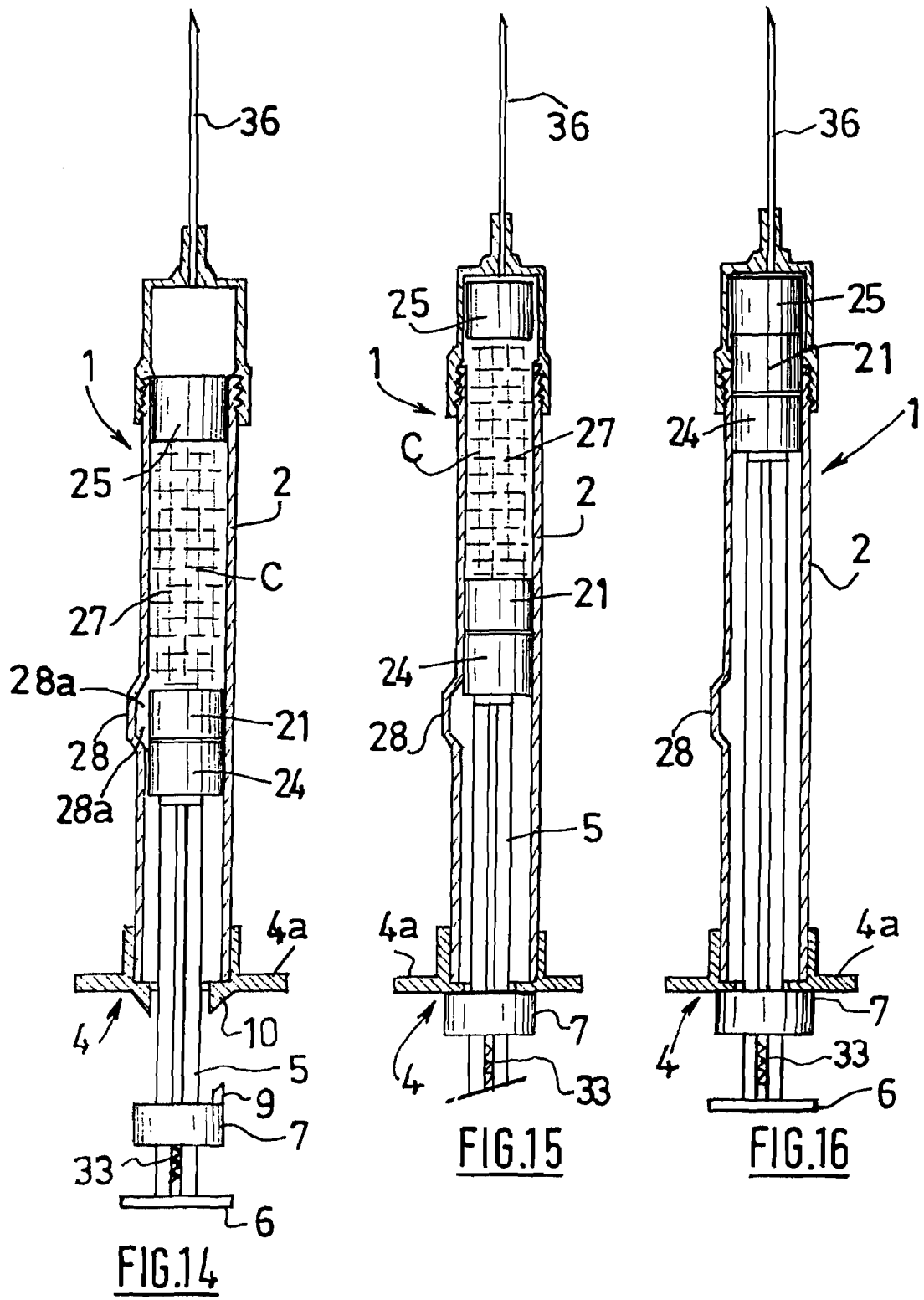

CONTAINER, DEVICE AND METHOD TO STORE AND EXPEL A PRODUCT

The present invention relates to a container used to store and expel a product, this container being more particularly suitable in the medical field for the preparation of a product necessitating several successive steps. The present invention also relates to a device comprising such a container and a method of using such a container.

In the present application, the "distal end" of a component or device means the end furthest from the user's hand, and "proximal end" the end nearest to the user's hand. Similarly, the present application uses the expression "distal direction" to refer to the direction of injection, and "proximal direction" to denote the opposite direction.

In the medical field, the process of administering a product to a patient can be performed using an administration device which may contain a cartridge, a syringe or similar. This administration device may be chosen among the injection devices commonly used to inject a medicinal product in the body of a patient or among any other suitable administration devices such as oral or similar devices. Whatever the administering device is, the process of preparing or administering a product may involve several successive steps. For example, in the most common case in which a nurse has to inject the content of a syringe into a patient, she usually begins by purging said syringe to ensure that any air potentially present at the distal end of the syringe body when the syringe is in the storage position has been expelled before the needle is inserted into the patient's skin. For this purpose the nurse usually begins by applying an initial pressure to the rod of the plunger of the syringe in order to propel the injectable product to the distal end of the needle.

However, to avoid wasting too much injectable product and so giving the patient too small a dose, the nurse must be careful not to inadvertently continue pushing the plunger rod for too long.

Once the syringe is purged, the nurse can proceed to the second step, the proper injection. This step itself may sometimes be divided into several successive steps, as for example where several doses of the injectable product are to be injected one after the other. The administration of certain particular medicinal products also demands a succession of precise steps in order to prepare the product. Thus, in the case of anti-cancer products such as Taxotere® for example, the active principle must be stored separately from the solvent with which it should only be mixed just before the time of injection. Injection devices such as syringes provided with two separate chambers, one containing the active principle and the other its solvent, are used for this purpose. The nurse first pushes on the plunger rod, whereupon the active principle travels along a by-pass system and enters the chamber containing the solvent. The nurse must than pause while mixing together—e.g. by shaking the injection device—the active principle and the solvent to prepare the medicinal product that is to be injected. If the nurse fails to stop pushing the plunger rod just after the active principle has reached the solvent in its chamber, some of the solvent or of the active principle or of the medicinal product may be expelled unintentionally from the injection device. This may compromise the quality of the reconstitution of the medicinal product and/or lead to a smaller amount of the medicinal product being administered.

Once the medicinal product is formed, the nurse can proceed to the second step, that of proper injection, by inserting the needle of the injection device in the patient's skin and once again by applying pressure to the plunger rod. This step may itself be divided into several steps to inject several doses as already seen.

Thus, in the cases mentioned above, it is particularly important that the plunger rod be stopped exactly and precisely at the end of the first step.

An injection device suitable for cases where successive doses have to be injected into a patient is disclosed in document U.S. Pat. No. 5,328,486. This comprises a syringe fitted with a delivery-controlling button that can be moved manually along the plunger rod. When the delivery-controlling button reaches the flange of the syringe body, the nurse knows that the desired dose has been administered. This delivery-controlling button can also be used to net a first step position of the plunger rod for example to purge the injection device.

However, such delivery-controlling button, being easily movable by hand at any time, is no guarantee that:
the delivery-controlling button will be precisely set by the user before the use of the injection device to define accurately the first step position, and/or that
the user will not inadvertently modify the setting of the first step position during the use of the injection device before reaching the first step position.

The same type of problem can be encountered in other technical fields such as those for which the mixing of two components is required before use of the obtained product such as for example the glues. Indeed, for some glues, components have to be stored in separate compartments and later being mixed just before the use of the glue, following a process similar to the one used for the injection operation previously described.

Documents CH 279779 and FR 2881052 describe injection devices comprising a body receiving a product, a pusher and a locker for locking the movement of the pusher. There is therefore still a need for a safe administration device with which any user would be sure not to inadvertently move the plunger rod past the limit set for the preparatory first step of an administration operation, this administration device allowing to move said plunger rod again for at least one or more subsequent steps, and in particular for the administration of one or several doses. The preparatory step can be a mixing step, a purging step or any other similar step required before the preparation of the product.

There is also a need for a method to use such a container.

In the present application, "administration" means injection, spraying or any similar expelling way and "plunger rod" means any part movable in the body containing the product to be administered and designed to expel the product outside of the container. The present invention meets these needs by providing a novel administration device equipped with lockable arresting means enabling to ensure that the plunger rod has a reliable predefined first step position, preventing any unsetting of the first step position displacement and being unlockable automatically when the first step position is reached in order to allow a controlled continuation of the movement of said plunger rod.

The present invention also meets these needs by providing a method enabling to use such a container, this method enabling, before use, an accurate setting of a first step position and, the insurance that this setting will not be manually modified before being reached.

The present invention relates to a container comprising at least
a body forming at least one cavity designed to contain at least one product, a pusher movable with respect to said body between at least an "initial position" and an "end-of-use position" to expel at least part of said product from said body, a locker located on said pusher and forming an abutment so as to be able to abut against said body between said "initial position" and "end-of-use position"

locking means capable of, temporarily, lock said locker on said pusher, at least in the proximal direction relative to said pusher, so as to define a "locker locking position" and, when said pusher abuts against said body via said locker, define a "pusher locking position", unlocking means designed so that their triggering causes the release of said locking means so as to allow i) said locker to be displaced proximally relative to said pusher and ii) said pusher to be moved past said "pusher locking position" toward said "end-of-use position", which container is characterized in that:

said locking means are located partially on said pusher and partially on said locker, said unlocking means comprising at least one bearing surface designed for automatically releasing said locking means in said "pusher locking position" upon distal pressure exerted on said pusher.

The container of the invention allows the user to perform any preparatory step without having to fear to inadvertently move distally the pusher and therefore compromise the future administration of the product.

In an embodiment, the container of the invention further comprises setting means designed to be:

capable of, temporarily, block said locker on said pusher, at least in the proximal direction relative to said pusher, so as to define a "locker setting position" and, when said pusher abuts against said body via said locker, define a "pusher setting position", capable of being manually triggered and then allow said locker to be displaced proximally relative to said pusher and said pusher to be moved past said "pusher setting position" toward said "end-of-use position".

In an embodiment of the invention, said locking means and/or setting means comprise at least one partially elastically deformable stop located on said locker or pusher and able to cooperate with said pusher or locker to define said "pusher locking position" and/or "pusher setting position", said deformable stop being able to be deformed, in said "pusher locking position" and/or "pusher setting position" to allow at least the distal displacement of said pusher relative to said body.

In an embodiment of the invention, said deformable stop can be manually deformed to release said setting means.

In an embodiment of the invention, said locker or pusher comprises at least one flexible leg bent toward said pusher or locker with which it is engaged at least by friction, said flexible leg defining at least part of said locking means and/or setting means.

In an embodiment of the invention, said locker comprises at least one longitudinal wall elastically deformable between an "engaged position" in which it is engaged at least by friction with said pusher and a "released position" in which it releases said pusher, said longitudinal wall defining at least part of said locking means and/or setting means.

In an embodiment of the invention, said locking means and/or setting means comprise at least one movable stop located on said locker or pusher and able to cooperate with said pusher or locker to define said "pusher locking position" and/or "pusher setting position", said movable stop being able to be tangentially moved relative to said pusher, in said "pusher locking position" and/or "pusher setting position" to release at least the distal displacement of said pusher relative to said body.

In an embodiment of the invention, said locking means and/or setting means comprise at least one breakable stop located on said locker or pusher and able to cooperate with said pusher or locker to define said "pusher blocking position" and/or "pusher setting position", said breakable stop being able to be broken by the action of said unlocking means and/or manually, in said "pusher locking position" and/or "pusher setting position" to release at least the distal displacement of said pusher relative to said body.

In an embodiment of the invention, said locker is mobile in rotation with respect to said pusher.

In an embodiment of the invention, said unlocking means comprise at least one bearing surface capable of, when said locker is pressed against said body in said "pusher blocking position", deforming said deformable stop and/or moving said movable stop and/or breaking said breakable stop to release said locking means.

Preferably, said deformable stop and/or movable stop and/or breakable stop comprise at least an inclined surface, said bearing surface being also inclined in order to, when said locker is pressed against said body in said "pusher blocking position", said inclined surface and bearing surface cooperate with each other to deform and/or move and/or break said deformable stop and/or movable stop and/or breakable stop and release said locking means.

In an embodiment of the invention, said deformable stop and/or movable stop and/or breakable stop comprise at least one tooth located either on said locker or on said pusher, and at least one indent correspondingly located either on said pusher or on said locker, said tooth being engaged in said indent before the release of said locking means and/or setting means.

In an embodiment of the invention, said locker defines a recess in which at least a part of the cross section of said pusher is housed. Said locker may be provided in its recess with at least one radial tooth designed to engage with an indent on said pusher, said radial tooth and indent defining at least in part said setting means and/or said locking means.

In an embodiment of the invention, said locker is being provided with at least one flexible radial tab designed to engage with a spur on said pusher and to define at least in part said locking means, and in that said radial tab is continued at its distal end by a deactivating tab designed to engage with said body to disengage said radial tab from said spur to unlock said locking means, said deactivating tab defining at least part of said unlocking means.

In an embodiment of the invention, at least part of the cross section of said pusher has a H shape, said recess of said locker is opened and has a C shape complementary to a first side of said H shape engaged in said C shape, the second side of said H shape receiving a flexible leg extending from said locker in order to press said C shape against said H shape of said pusher and block said locker on said pusher.

In an embodiment of the invention, the unlocking means are designed to prevent their manual triggering before reaching said "pusher locking position". For example, at least part of the unlocking means are embedded in the locker in order to be manually inaccessible.

The container of the invention is therefore particularly safe.

In an embodiment of the invention, said locker is designed to be able to, before the use of said pusher, be manually adjusted on said pusher to set said "locker locking position".

In an embodiment of the invention, said locker has a symmetry of revolution about the longitudinal axis of said pusher.

Such an embodiment is particularly advantageous in that the user doesn't need to position the container in a specific orientation before use. Such an embodiment is therefore very easy and simple to use.

In an embodiment of the invention, said locker and said pusher are respectively being provided with two sets of radial teeth and indents, one "setting set" for the setting means and one "locking set" for the locking means, the setting and locking sets being located at a different distance from said pusher axis to allow:
- to keep the engagement of both said locking and setting sets before reaching the "pusher blocking position", and
- to keep the engagement of said setting set after the release in said "pusher blocking position" of said locking set up to the manual release of said setting means.

In an embodiment of the invention, said locker is made of at least two parts, one part comprising at least part of the locking means, the other part comprising at least part of the setting means.

A further aspect of the present invention is a device, for example a medical device, characterized in that it comprises a container as described above, in which said body is a barrel, said pusher is a plunger rod and said locker is a button movable at least in translation along said plunger rod.

Preferably, the device, in particular medical, of the invention comprises at least a first plug, a second plug and a third plug, all contained within said barrel, said first plug being in a more proximal position than said second plug and designed to be linked to said pusher, said third plug being in a more distal position than said second plug, said first, second and third plugs being movable in translation at least between:
- a "said initial position", in which said first plug and said second plug define a first chamber containing a substance A, and said second plug and said third plug define a second chamber containing a substance B,
- a "by-pass position", in which said first, second and third plugs are located distally forward from the "initial position", said second plug being located in a transfer zone provided for this purpose within said body to allow the transfer of substance A from said first chamber to said second chamber,
- a "mixing position" corresponding to said "pusher locking position" and in which all of substance A has reached, via the transfer zone, all of substance B in said second chamber, said first plug having moved in the distal direction until it has made contact with said second plug, the third plug having not moved significantly, the distance between said locking means and said unlocking means in the "by-pass position" being the same as the distance traveled by said first plug from said "by-pass position" to said "mixing position",
- an "open position" in which said first, second and third plugs have been distally moved forward from said "mixing position", said third plug being located in a wider zone provided to allow said substances A and B to by-pass said third plug.

A further aspect of the invention is a method, in particular non therapeutic, for using a device as described above, characterized in that, after said "open position", said first, second and third plugs are movable to a "pusher setting position" corresponding to said "pusher setting position" and in which said first and second plug have moved toward said third plug compared to the open position, the distance between said setting means and said body in the "open position" being the same as the distance traveled by said first and second plug from said "open position" to said "pusher setting position".

In an embodiment of the invention, after said "open position", said first, second and third plugs are movable to an "end of use position" in which, the first, second and third plug have reached the distal end of said body.

A further aspect of the invention is a method for using a container containing at least a product to be at least in part expelled from said container, said method comprising at least the following successive steps:
a) a container as described above is provided, said container being in the "initial position" with said locker in said "locker locking position" on said pusher,
b) said pusher is pushed distally relative to said body up to the "pusher locking position" and up to the release of said locking means,
c) said setting means are then manually released,
d) said locker is displaced proximally on to said pusher up to said "locker setting position",
e) said pusher is moved distally relative to said body up to said "pusher setting position".

A further aspect of the invention is a non therapeutic method for using a container in particular for the preparation of a product, said method comprising at least the following successive steps:
a) a container as described above is provided, said container being in the "initial position" with said locker in said "locker locking position" on said pusher,
b) said pusher is pushed distally relative to said body up to the "pusher locking position" and up to the release of said locking means,
c) said setting means are then manually released,
d) said locker (7) is displaced proximally on to said pusher up to said "locker setting position",
e) said pusher is moved distally relative to said body up to said "pusher setting position".

In an embodiment of the invention, said locking means define a said "locker locking position" which corresponds to a "locker setting position" in order to, when the locking means are automatically released in said "pusher setting/locking position", have the setting means prevent the pusher from being moved passed said "pusher setting/locking position" until manual release of said setting means.

In an embodiment of the invention, after the triggering of said unlocking means and release of said locking means, said locker is able to be taken away from said body.

In one embodiment of the method of the invention, the product is a medicine to be stored. In another embodiment of the method of the invention, the product is a non medical product selected from the group comprising a glue, an ink, a food product.

The container and device of the invention will now be further described in reference to the following description and attached drawings in which:

FIGS. 11 to 16 are cross section views illustrating the different steps in the use of a variant of a container according to the invention.

In order to simplify the understanding of the invention, the following description will be limited to a container used in a medical device and more specifically an injection device. It is to be understood that the invention also covers any similar container usable in the same medical field or any other technical fields.

Figure 1:
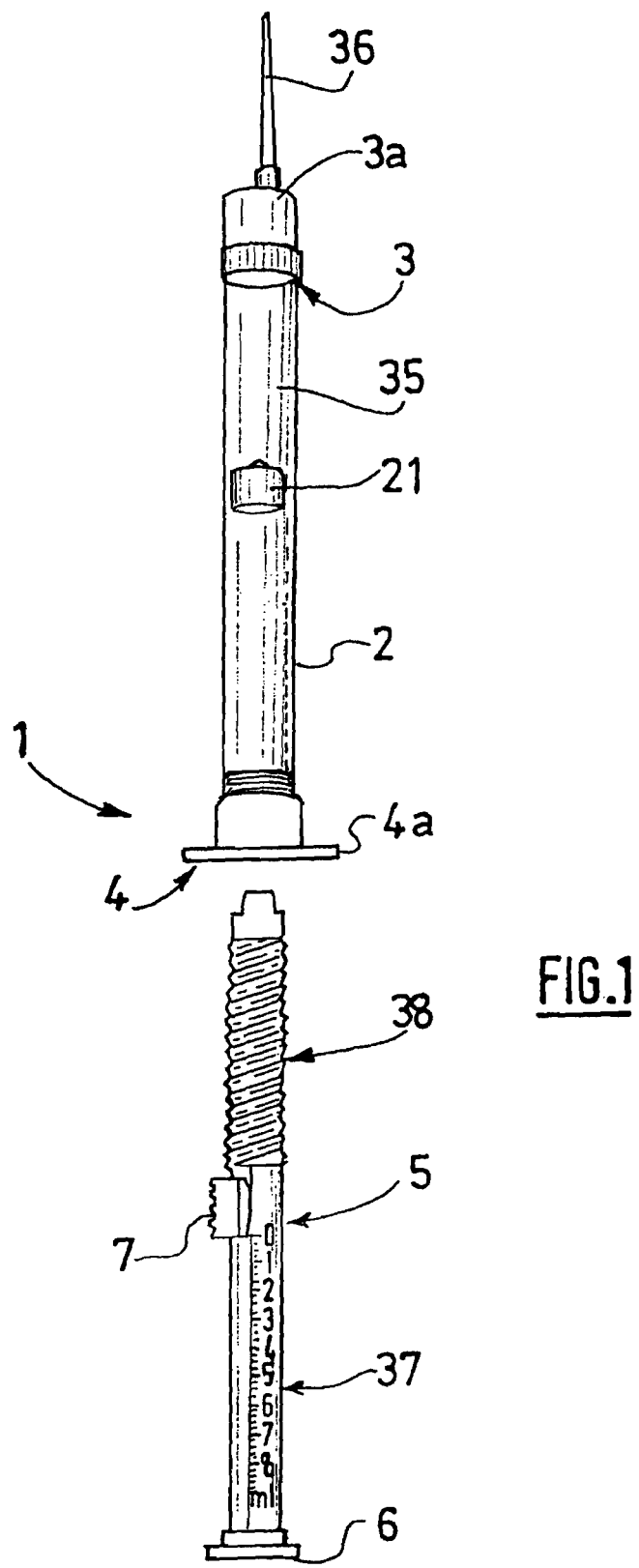
FIG. 1 is a side view of a container according to the invention.

In reference to FIG. 1, there is shown a container 1 according to the invention, in this example a medical device, more specifically an injection device 1 that can be used for administering a product 35. The product 35 to be administered may be any drug such as contrast media or medicine that may be administered to a patient, via injection or other ways. The injection device 1 of the invention of FIG. 1 comprises a tubular body 2 with a distal end 3 having an opening 3a defined thereat and a proximal end 4. As shown on FIGS. 1 and 3, the proximal end 4 of the body 2 preferably comprises a flange 4a. Such a flange 4a allows an easy grasping and handling of the injection device 1. As appears from FIG. 3, the proximal end 4 of the body 2 is provided with a bearing part 10, protruding in the proximal direction.

The opening 3a of the injection device 1 shown on FIG. 1 is provided with a needle 36. The injection device 1 is therefore preferably an injection device for administering a product 35 by injection.

Alternatively, the opening 3a could be left open or provided with a spraying system, and the medical device of the invention could be a device for administering a product 35 via oral or nasal route like a oral spray device or a nasal spray device. The distal end 3 could also be equipped with a "luer" type connection enabling the assembling of different type of extremities for example to allow the aspiration of a product 35 from a vial with a large diameter needle before its injection with a small diameter needle.

As shown on FIG. 1, the body 2 is intended to receive the product 35 to be administered. A pusher, in this example a plunger rod 5, movable with respect to said body 2 is provided. As appears from FIGS. 1 and 4, the proximal portion 37 of the plunger rod 5 has a section having roughly the shape of a cross with one of the branch having the shape of a "T" to define a "H" shape, and the distal portion 38 of the plunger rod 5 is threaded: such an embodiment allows a smoother and controlled distal movement of the plunger rod 5 when the threaded portion 38 is screwed on the internally threaded part (not shown) of the flanges 4a. Alternatively, the plunger rod 5 could be a full classical plain rod, for example with a circular cross section on the totality of its length, or a rod with a section having the shape of a cross on the totality of its length like shown on FIGS. 11-16.

Figure 3:
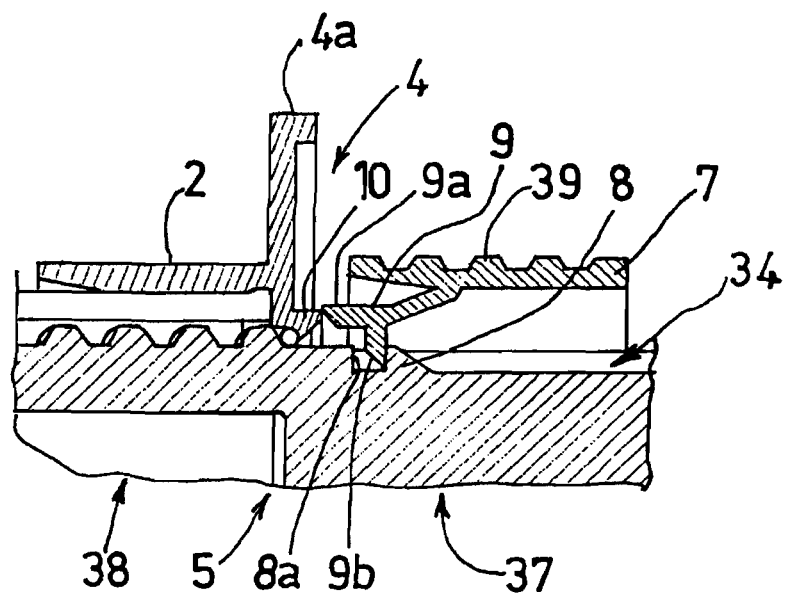
FIG. 3 is a partial cross section view of the container seen in FIG. 1 showing the locking means and the unlocking means in the "pusher locking position" at the moment when the locking means come into contact with the unlocking means.

As shown on FIG. 3, the proximal portion 37 of the plunger rod 5 is provided with a fixed stop 8 or spur. The fixed stop 8 defines with the proximal end of the distal portion 38 of the plunger rod 5 a groove 8a.

Figure 4:
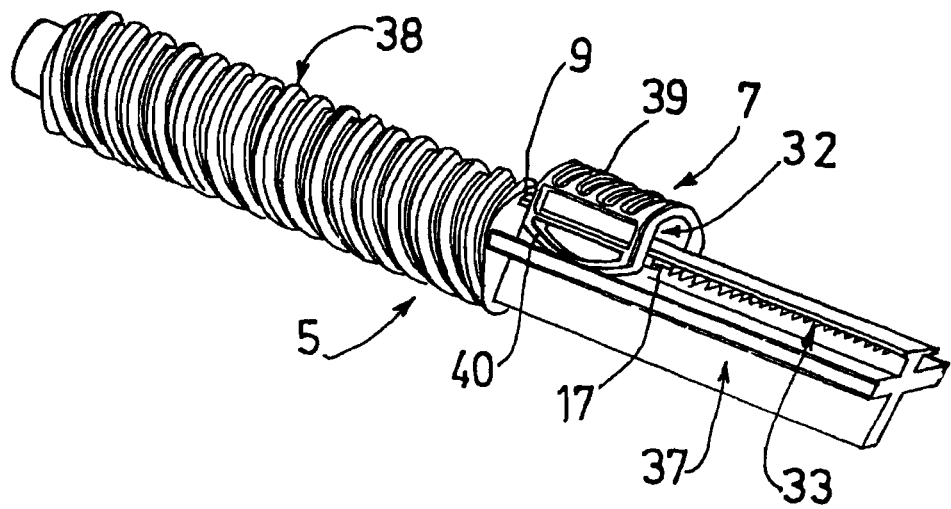
FIG. 4 is a partial perspective view of the container shown in FIG. 1 showing the locker in place on the pusher.

As shown on FIG. 4, the proximal portion 37 is further provided with a plurality of indents 33 located along the longitudinal direction of the "T" shape branch of the plunger rod 5 and extending toward the axis of the plunger rod 5.

The injection device 1 of the invention of FIGS. 1-4 further comprises a plug 21 which is movable in the body 2 and intended to be moved in the distal direction by said plunger rod 5, upon pressure exerted on the head 6 of said plunger rod 5, between an "initial storage position", in which the injection device 1 is provided to the user, and an "end-of-use position", the movement of said plug 21 between said positions causing passage of some of the product 35 towards and/or through the opening 3a at the distal end 3 of the body 2. The "end-of-use position" is situated further forward in the distal direction than the "initial storage position" and is preferably the position where the plug 21 reaches the distal end of the body 2, for instance at the end of injection of the totality of the product 35 in the embodiment shown on FIG. 1. The "end-of-use position" can also be a position in which a predefined quantity of the product 35 has been expelled from said body 2.

On the embodiment of FIG. 1, the plug 21 is a self standing piston and is not permanently fixed to the distal end of the plunger rod 5. Such a plug 21 is coupled to the distal end of the plunger rod 5 at least in the distal direction during the injection operations. Alternatively, the distal end of the plunger rod 5 may be threaded or snap fit inside the plug 21, either permanently or at the time of use.

The injection device 1 of FIG. 1 is provided with a locker 7 capable of cooperating with the plunger rod 5 and the flanges 4a of the body 2 to temporarily prevent, in at least the distal direction, the movement of said plunger rod 5 with respect to said body 2 in order to act as setting means and/or locking means and define at least one "intermediate position" of said plug 21 between said "initial and end-of-use positions".

The locker 7 of the injection device 1 of FIG. 1 is intended to be provided on the proximal portion 37 of the plunger rod 5. This locker 7 is shown, alone, on FIGS. 2A and 2B, and in place on the proximal portion 37 of the plunger rod 5, on FIGS. 3 and 4. As appears from these figures, the locker 7 has substantially the global shape of half a cylinder and defines a recess 32 in which at least part of the cross section of the plunger rod 5 is housed when said locker 7 is in place on said plunger rod 5. As shown on FIG. 2B, the recess 32 defines bearing surfaces 42 designed to bear on two lateral branches of the cross shaped proximal portion 37 of the plunger rod 5 so as to guide the locker 7 along the plunger rod 5 during its movement relative to said plunger rod 5.

Figure 2A:
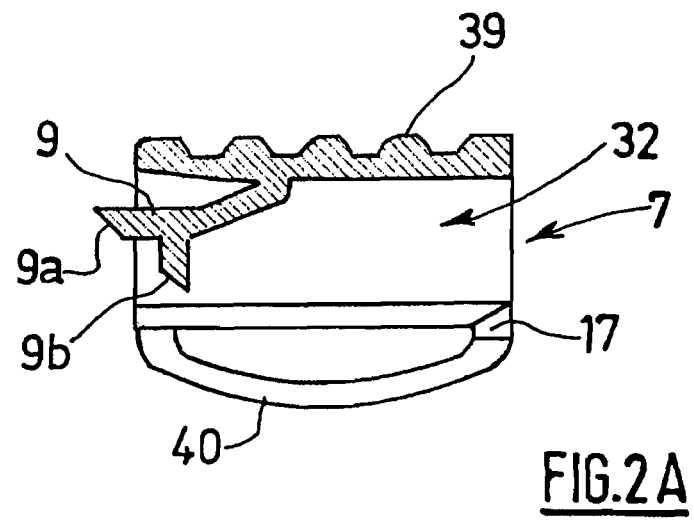
FIG. 2A is a cross section view of the locker of the container shown in FIG. 1 showing part of the locking means and setting means.
Figure 2B:
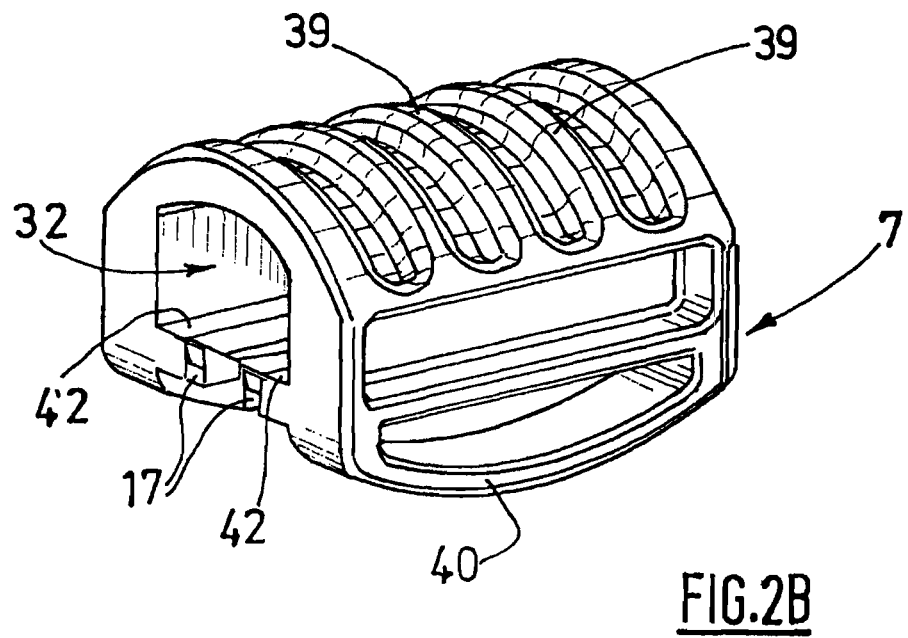
FIG. 2B is a perspective view of the locker of the FIG. 2A showing the setting means.

As shown on FIGS. 2A, 2B and 4, the locker 7 further comprises at least part of locking and setting means.

The locker 7 comprises a radial tooth 17 intended, as described hereafter, to engage with indent 33 to set the position of the locker 7 on the plunger rod 5. In addition, as shown on FIGS. 2A and 4, the locker 7 comprises two lateral flexible legs 40 elastically deformable in order to press against the two lateral branches of the cross shaped proximal portion 37 of the plunger rod 5 so as to keep the radial tooth 17 engaged with the indent 33 and the locker 7 in a fixed "locker setting position" relative to the plunger rod 5.

As seen on FIG. 2B, the recess 32 is opened and has a C shape. As seen on FIG. 4, the C shape of the recess 32 is complementary to a first side of said H shape of the plunger rod 5, said H shape being engaged in said C shape. The second side of the H shape of the plunger rod 5 receives the flexible leg 40 extending from the locker 7 in order to press said C shape against said H shape of the plunger rod 5 and block the locker 7 on the plunger rod 5.

Due to the pressure applied by the flexible legs 40 on the plunger rod 5, the radial tooth 17 will stay engaged with the indent 33 even when the locker 7 will abut against the flanges 4a of the body 2, defining then a "pusher setting position". The radial tooth 17, indent 33, flexible legs 40, plunger rod 5 and flanges 4a act as the setting means which prevent the locker 7 from moving inadvertently on the plunger rod 5. As it will be described after, the setting means can be released manually to allow the further displacement of the plunger rod or pusher 5 relative to the body 2.

As shown on FIG. 2A, the locker 7 also comprises a radial tab 9 which is flexible and provided with a longitudinal tongue 9a and with a radial tongue 9b. In this example, the radial tab 9 and the radial tooth 17 are situated on either side of said recess 32 relative to the longitudinal axis of said locker 7.

As shown on FIG. 3, radial tongue 9b of the radial tab 9, is in abutment against the fixed stop 8 by engagement in the groove 8a so as to keep the locker 7 in a "locker locking position". This "locker locking position" is maintained by the bearing surfaces 42 (not visible on this figure) which bear on the two lateral branches of the plunger rod 5. The radial tongue 9b, the fixed stop 8, the bearing surfaces 42 and the plunger rod 5 act as locking means which prevent the locker 7 from moving inadvertently on the plunger rod 5, particularly in the proximal direction relative to the plunger rod 5. As it will be described after, the longitudinal tongue 9a of the locker 7 and the bearing part 10 of the body 2 are able to act as unlocking means to automatically release the locking means in the "pusher locking position" when the longitudinal tongue 9a abuts against the bearing part 10. In this "pusher locking position" the locker 7 is maintained fixed on the pusher 5 by the setting means up to their manual release.

As shown on FIGS. 2A and 2B, the locker 7 further comprises bulges 39 intended to provide an adhering surface, for example for a finger of the user, in order to manually move said locker 7 along the longitudinal direction of the plunger rod 5.

In an embodiment not shown, the locker 7 is designed to prevent the manual triggering of the unlocking means. For example, the locker 7 is longer so as to prevent the longitudinal tongue 9a of the movable stop 9 to protrude from the locker 7. Then the user cannot manually radially and outwardly deflects the longitudinal tongue 9a to disengage the radial tongue 9b from the groove 8a and in consequence disengage the radial tab 9 from the fixed stop 8.

In a preparatory step, the user causes the plunger rod 5 to move distally from the initial position in which the locker 7 is not in contact with the body 2 to a first intermediate position, shown on FIG. 3, in which the locker 7 is in contact with the body 2 for the unlocking means to be able to release the locking means. Said preparatory step may be the purge of the injection device 1 to ensure that any air potentially present at the distal end 3 of the body 2 has been expelled before the needle 36 is inserted into the patient's skin. Alternatively, said preparatory step may be the step of reconstitution of a medicine, as will be described in relation with FIGS. 11-16 of the present application.

During this preparatory step, the locking means and setting means prevent the locker 7 from being displaced relative to the plunger rod 5, in the proximal and distal directions, and maintain it in its "locker locking position" which in this example also corresponds to the "locker setting position". In consequence, the locker 7 can not move, neither in the proximal direction nor in the distal direction relative to the plunger rod 5. The setting of possible displacement of the plunger rod 5 relative to the body 2 is therefore predetermined, the position of the locker 7 on the plunger rod 5 being fixed. The reliability of the container 1 is improved when, as described before, the unlocking means are inaccessible and the locking means cannot be unsettled manually.

When the plunger rod 5 arrives close to the "pusher locking position", as shown on FIG. 3, the radial tab 9, by way of the longitudinal tongue 9a of the locker 7, comes in abutment against the bearing part 10 of the proximal end 4 of the body 2. The distal movement of the plunger rod 5 is therefore stopped in the "locker locking position" and the user gets the information that the preparatory step is completed.

When the preparatory step is completed, for example the purge of the injection device 1 or the reconstitution of the medicine, the plug 21 is in an intermediate position (not shown), and the user is ready to perform the next step, for instance the insertion of the needle 36 in the injection site and the injection of at least part of the product 35.

The user then applies a further distal pressure on the plunger rod 5 and the bearing part 10, which faces the radial tab 9, cooperates with the longitudinal tongue 9a of the locker 7 to deforms said flexible radial tab 9 and therefore disengages its radial tongue 9b from the fixed stop 8 and the groove 8a. The radial tongue 9b is then allowed to overcome the fixed stop 8. The bearing part 10 therefore acts as automatic unlocking means designed to release the locking means 8, 9, in the "pusher locking position" which corresponds to the intermediate position, upon distal pressure exerted by the user on the plunger rod 5.

When the radial tongue 9b has passed the fixed stop 8, it can freely deflect in the longitudinal groove 34 located in the plunger rod 5 where it can freely be displaced.

In the embodiment shown on FIGS. 1-4, the fixed stop 8 is provided on the plunger rod 5 and the movable stop 9 is provided on the locker 7, said fixed and movable stops 8, 9 being designed to engage with each other while locked and said radial tab 9 being deformed when acted upon by the bearing part 10.

Figure 5:
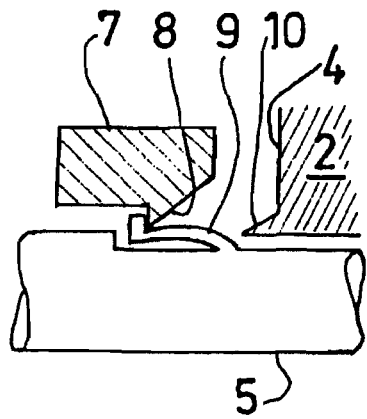
FIG. 5 is a partial cross section view of a variant of the container according to the invention.

In an embodiment of the invention shown on FIG. 5, the fixed stop 8 is provided on the locker 7, and the radial tab 9 is provided on the plunger rod 5.

In another embodiment of the invention, not shown, the locking means comprise at least one breakable element designed to be broken by the action of the unlocking means when in the "pusher locking position" and when a distal pressure is applied to the plunger rod.

In the embodiment of FIGS. 1-4, the locker 7 may be used, after the "pusher locking position", as setting means to set the quantity of product 35 to be injected. To do so, when the "pusher locking position" is reached, the user can manually press on the locker 7 to release the setting means. The pressure applied deforms the lateral skirt 40 and allow the disengagement of the radial tooth 17 from the indents 33. The user can then moves the locker 7, past the "locker locking position", in the proximal direction relative to the plunger rod 5, up to a "locker setting position" corresponding to the wanted injection setting.

The locker 7 is adjustable in position along said plunger rod 5 and may be immobilized at a given height defining, between the "locker locking position" and the "end-of-use position", a "pusher setting position", thanks to the cooperation of the radial tooth 17 of the locker 7 with the indents 33 defined on the proximal portion 37 of the plunger rod 5. When the dose setting is reached, the user releases the pressure from the locker 7 to allow the radial tooth 17 to engage indents 33 so as to set an injection dose. The indents 33, the tooth 17, the locker 7 and the body 2 when in abutment, therefore act as setting means. The indents 33 are designed as a rack such as allowing the release of the tooth 17 by hand when the locker 7 is manually pressed against the plunger rod 5. The locker 7 can then be moved in the proximal direction relative to the plunger rod 5. The rack of indents 33 allow an accurate continuous setting of the dose to be injected.

In another embodiment not shown, the plunger rod can have only one or a limited number of indents in order to have defined and limited number of possible "locker setting positions".

In the embodiment of FIGS. 1-4, the tooth 17 is provided on the delivery-controlling locker 7 and the indents 33 are provided on the plunger rod 5, the tooth 17 being engaged with the indents 33 when the pressure on said delivery-controlling locker 7 is released.

In an embodiment of the invention not shown, the tooth is provided on the plunger rod and the indent are provided on the locker.

Figure 6:
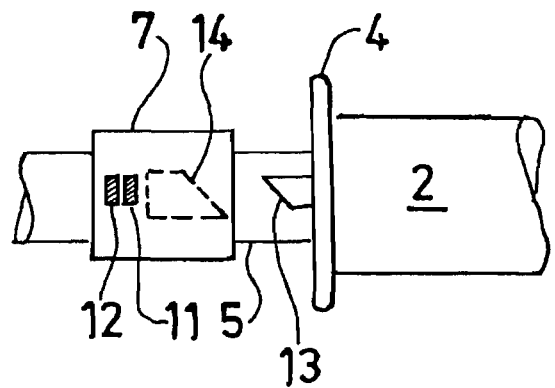
FIG. 6 is a partial side view of another variant of the container according to the invention.

On FIG. 6 is shown partially a variant of the injection device 1 of the invention, wherein the locker 7 contains a movable stop 11 and is designed so that, at least in the "pusher locking position", to be able to be moved tangentially relative to the fixed stop 12 located on the plunger rod 5, to release the locking means.

As appears from FIG. 6, the proximal end 4 of the body 2 comprises a first inclined surface 13. The locking means comprises a locker 7 provided with a movable stop 11 and the plunger rod 5 is provided with a fixed stop 12. The locker 7 is provided, on its inner wall, with a second inclined surface 14, shown in dotted line on FIG. 6. The movable stop 11 and the second inclined surface 14 are therefore coupled to each other.

In the initial storage position, the movable stop 11 is in abutment on the fixed stop 12 and the locker 7 is prevented to move at least in the proximal direction relative to the plunger rod 5. The movable stop 11 and the fixed stop 12 act as locking means of the locker 7 in the proximal direction in a "locker locking position".

When the user applies a distal pressure on the plunger rod 5, just before the "pusher locking position" is reached the first and the second inclined surfaces 13, 14 come in contact with each other and act upon each other to turn the locker 7 relative to the plunger rod 5, and in consequence turn the movable stop 11 relative to the fixed stop 12. The locking means are released, the locker 7 is no more prevented from moving by them and the user can manually move it in the proximal direction so as to allow the plunger rod 5 to pass the "pusher locking position" and to further move in the distal direction.

In such an embodiment as shown in FIG. 6, the setting means (not shown) can be released by a tangential displacement.

Figure 7:
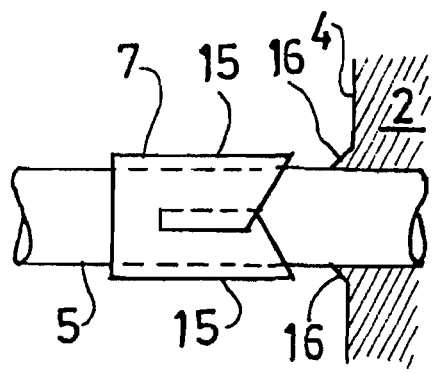
FIG. 7 is a partial side view of another variant of the container according to the invention.

On FIG. 7 is shown a variant of the injection device 1 of the invention, in which the plunger rod 5 comprises two or more longitudinal walls 15, elastically deformable, forming a sort of extendible envelope around the plunger rod 5, said walls 15 being capable of bending radially and tending to compress the plunger rod 5. The walls 15 are then engaged by friction with the plunger rod 5 and define at least part of the locking means. The distal end of the locker 7 comprises a tapered extremity. The proximal end 4 of the body 2 comprises a tapered bearing surface 16 protruding in the proximal direction.

In the locked position, as shown on FIG. 7, the walls 15 are engaged by friction with the plunger rod 5. When in the "pusher locking position", a distal pressure is applied to the plunger rod 5, the bearing surface 16 comes in contact with the tapered extremity of the walls 15 and deforms said walls 15 causing them to bend radially outwardly and to be disengaged from the plunger rod 5. The locking means, formed by the walls 15, the plunger rod 5 and the body 2 are therefore released and the user can move the locker 7 in the proximal direction so as to allow the further distal movement of the plunger rod 5.

In an embodiment of the invention not shown, the locking means cooperate with each other by compression, or by any combination of stops, friction and compression.

Figure 8:
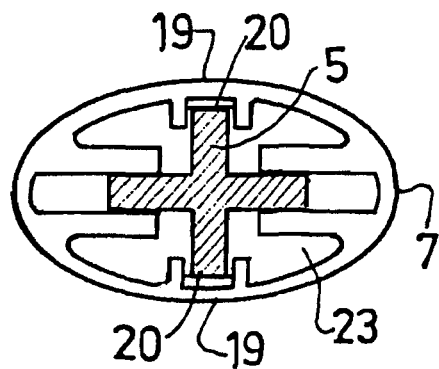
FIG. 8 is a cross section view of a variant of the locker of the container according to the invention, with the setting means engaged.
Figure 9:
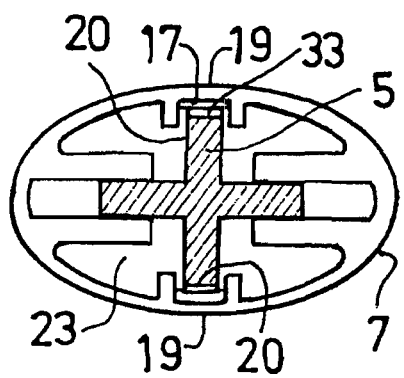
FIG. 9 is a cross section view of the locker of FIG. 8 with the setting means released.

On FIGS. 8 and 9 is shown a variant of the setting means of the locker 7 of the injection device 1 according to the invention, in which the setting means are at least partly elastically deformable between a "locker setting position" in which there is no manual pressure on them and they are coupled, by at least friction, to said plunger rod 5, and a "locker unsetting position" in which they are under manual pressure and can be manually translated relative to said plunger rod 5.

The locker 7 of FIGS. 8 and 9 comprises an elastically deformable wall 19 which may be formed of rubber for example. The plunger rod 5 of FIGS. 8 and 9 has a section having the shape of a cross, said cross having four branches 20. The locker 7 defines a recess 23 within said elastically deformable wall 19, in which the cross section of said plunger rod 5 is housed.

In the "locker setting position", as shown on FIG. 8, the elasticity of the elastically deformable wall 19 tends to put said recess 23 out of alignment with said plunger rod 5 so that it jams by friction as can be seen on FIG. 8, two of the branches 20 are in contact with the elastically deformable wall 19.

In the "locker unsetting position", as shown on FIG. 9, the user presses on the lateral sides of the locker 7, thereby deforming the wall 19 which bulges vertically, up and down, disengaging the ends of the two branches 20 which were in contact with said walls in the immobilized position. The recess 23 is then aligned with the plunger rod 5 and thus allows said locker 7 to be moved relative to said plunger rod 5.

In order to improve the efficiency of the setting means, the locker 7 and the plunger rod 5 can respectively comprise at least one radial tooth 17 and indent 33 (see FIG. 9).

Figure 10:
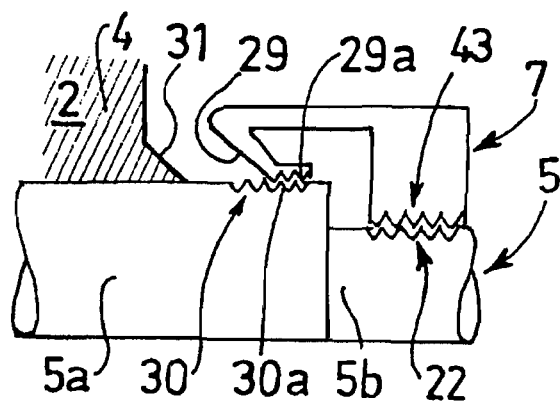
FIG. 10 is a partial cross section view of another variant of the container according to the invention.

On FIG. 10 is shown a variant of the injection device 1 of the invention in which at least a portion of the length of the plunger rod 5 has a symmetry of revolution about its longitudinal axis and is of circular cross section.

On FIG. 10, is shown partially the plunger rod 5 of an injection device 1 according to the invention. This plunger rod 5 comprises two circular portions 5a, 5b having different diameters, the diameter of portion 5b being smaller than the one of portion 5a. The portion 5a comprises locking fixed stops 30 under the form of a plurality of circular grooves 30a and the portion 5b comprises setting fixed stops 43 under the form of a plurality of circular groove 22. Said fixed stop 30, 43 therefore has symmetry of revolution about the longitudinal axis of the plunger rod 5.

The locker 7 is mounted on the circular portions 5a, 5b of the plunger rod 5 the locker 7 comprises a flexible leg 29 provided with a plurality of locking teeth 29a designed to cooperate with the fixed stops 30 to form part of the locking means and a plurality of setting teeth 43 designed to cooperate with the setting fixed stop 22 to form part of the setting means.

The proximal end 4 of the body 2 is provided with a tapered bearing surface 31 protruding from said body 2 in the proximal direction. Said tapered bearing surface 31 has a symmetry of revolution about the longitudinal axis of the plunger rod 5a. In another embodiment not shown, the tapered bearing surface 31 is not symmetrical about the longitudinal axis.

In the "locker setting position" which corresponds to the "locker locking position", shown on FIG. 10, the teeth 29a are engaged in the plurality of grooves 30a and block the locker 7 in its "locker locking position", the teeth 43 are engaged in the plurality of grooves 22 and block the locker 7 in its "locker setting position". During the preparatory step, the plunger rod 5 comes close to the body 2. In the "pusher locking position", not shown, the flexible leg 29 comes in contact with the tapered bearing surface 31 which, under distal pressure applied on the plunger rod 5 by the user, cooperates with said flexible leg 29 so as to deform it and disengage said teeth 29a from said grooves 30a. Because of the symmetry of revolution of both the fixed stop 30 and the unlocking means, i.e. the bearing surface 31, the locker 7 does not have to be positioned in a specific orientation relative to the plunger rod 5 when assembled.

After the automatic release of the locking means in the "pusher locking position", the setting means can be manually released to allow the displacement of the locker 7 to a setting position located proximally further on the plunger rod 5. Then the user can press on the plunger rod 5, for example to inject the product 35 in the injection site. When the plunger rod 5 reaches the "pusher setting position", with the locker 7 abutting against the body 2, the preset dose of product 35 has been injected. The setting means can be once again manually released to move the locker 7 in a second "pusher setting position" and so on.

On FIGS. 11 to 16 is shown a variant of the injection device 1 of the invention for which the preparatory step is a step of reconstitution of a medicine C from two substances A and B. On these figures is shown an injection device 1 for administering a product C (see FIG. 13). This injection device 1 comprises a tubular body 2 with a distal end 3 having an opening 3a provided with a needle 36. On FIGS. 11-14, the needle 36 is protected with a needle cap 41. The body 2 is provided at its proximal end 4 with a flange 4a and with a tapered bearing surface 10 protruding from said body 2 in the proximal direction. The body 2 comprises a transfer zone 28 of larger diameter, situated substantially at the middle of its length, the function of which will be explained later.

The injection device 1 is provided with a plunger rod 5 with a section having the shape of a cross. The injection device 1 is provided with locking means such as a fixed stop (not shown) similar to that of FIGS. 1-4 and located on the plunger rod 5, a locker 7 having a movable stop 9 similar to that of FIGS. 1-4. The cooperation of the fixed stop of the plunger rod 5 and of the locker 7 is similar to that described for FIGS. 1-4. The plunger rod 5 is provided with indents 33 located passed the fixed stop in the proximal direction. The locker 7 is also provided with teeth to cooperate with the indents and form part of the setting means.

The injection device 1 is further provided with a first plug 24, a second plug 21 and a third plug 25, all contained within the body 2, the first plug 24 being in a more proximal position than the second plug 21, the third plug 25 being in a more distal position than the second plug 21. The first, second and third plugs 24, 21, 25 are all movable translationally within the body 2 as will be explained later.

Figure 11:
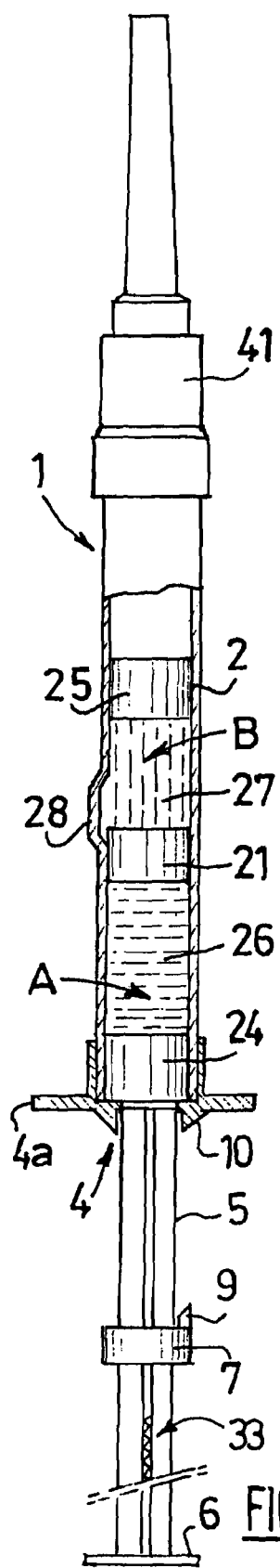

In the initial position, as shown on FIG. 11, the first plug 24 and the second plug 21 define a first chamber 26 containing a first substance A, and the second plug 21 and the third plug 25 define a second chamber 27 containing a second substance B. The two substances A and B are intended to be mixed in order to constitute a medicine C. This medicine C may be stored for a while before being injected into an injection site. In general, substances A and B have to be stored separately in order to avoid either problems of compatibility or of stability of the reconstituted medicine C. Alternatively, the medicine C may be reconstituted just before the injection.

The injection device 1 is provided to the user in the initial position shown on FIG. 11. In this position, the locker 7 is locked on the plunger rod 5 in the proximal direction by the locking means, in the same way as shown on FIGS. 3-4. In this position, the user can not move the locker 7 in the proximal direction.

Figure 12:
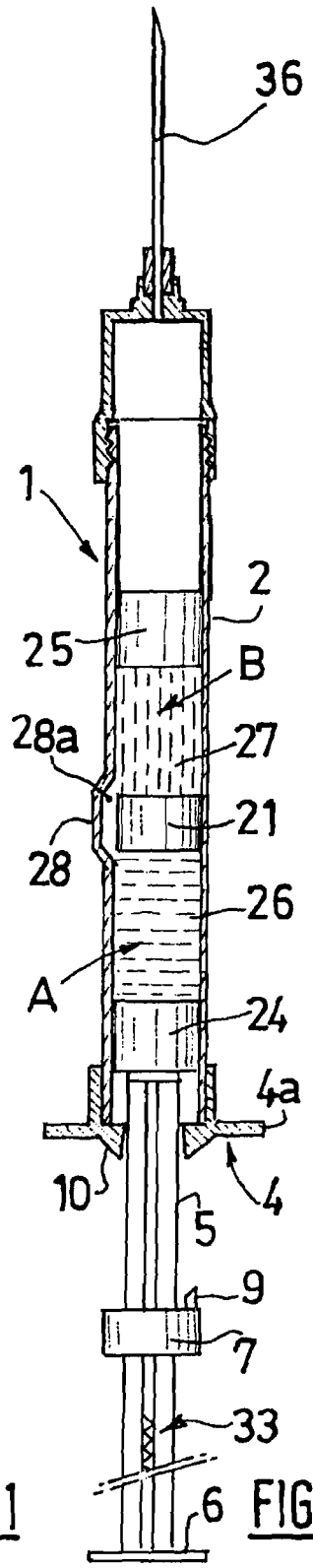

In order to complete the reconstitution step of the medicine C, the user removes the needle cap 41 and starts exerting a distal pressure on the plunger rod 5 and, as shown on FIG. 12, the first plug 24, the second plug 21 and the third plug 25 are moved distally until the second plug 21 reaches the transfer zone 28. Once the second plug 21 has reached the transfer zone 28 of larger diameter, the second plug 21 is no more in contact with the whole inner wall of the body 2 and a passage 28a is created within the transfer zone 28 of the body 2 for the substance A to flow from the first chamber 26 to the second chamber 27. As the user continues to apply a distal pressure on the plunger rod 5, the first plug 24 is moved distally until all of substance A has reached all of substance B in the second chamber 27, where the first plug 24 makes contact with the second plug 21 as shown on FIG. 13. The injection device 1 has then reached the "pusher locking position": the distance traveled by the first plug 24 from the initial position of FIG. 1 to the "pusher locking position" of FIG. 13 is the same as the distance separating, in the initial position, the radial tab 9 of the locker 7 from the tapered bearing surface 10 on the proximal and 4 of the body 2.

Figure 13:
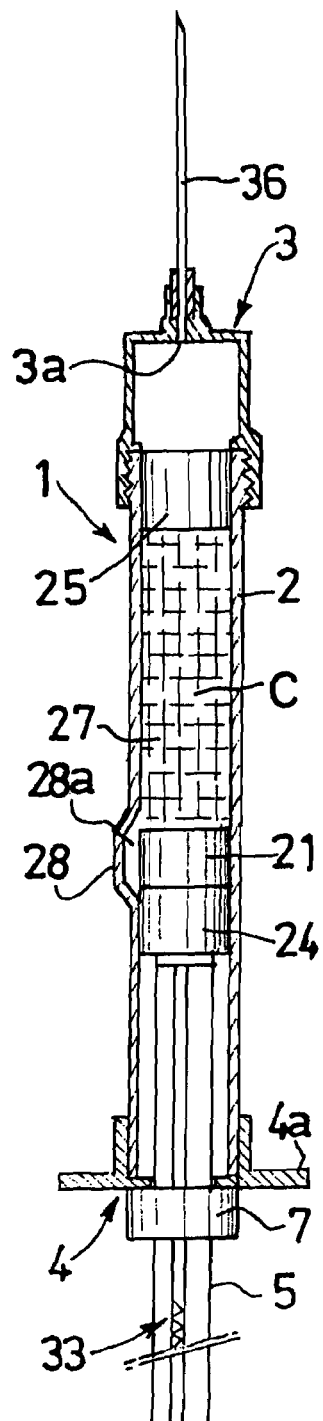

In the "pusher locking position", as shown on FIG. 13, under distal pressure exerted by the user on the plunger rod 5, the unlocking means automatically release the locking means. To do so, the bearing surface 10 comes in contact with the radial tab 9 and deform said radial tab 9 so as to release said locking means in the same way as explained for FIGS. 1-4. The teeth of the locker 7 are still engaged with the indents 33 of the plunger rod 5, acting as setting means blocking the locker 7 on the plunger rod 5.

As the plunger rod 5 cannot be further moved distally, the user knows that the intermediate position has been reached and he or she can for example agitate the injection device 1, if such a step is necessary for mixing substances A and B and reconstituting the medicine C, without any risk that the plunger rod 5 be inadvertently further moved distally. The reconstituted medicine C can be stored in the injection device 1 or used directly after the mixing.

The user is then able to manually release the setting means and move said locker 7 in the proximal direction, as shown on FIG. 14. On this FIG. 14, the user has manually moved the locker 7 in the proximal direction so as to immobilize it at a predetermined height of the plunger rod 5, in a first "locker setting position", by engaging a tooth (similar to the tooth 17 of FIGS. 1-4) of the locker 7 with the indent 33 of the plunger rod 5. The locker 7 is therefore immobilized on the plunger rod 5.

After having immobilized the locker 7 to the first "locker setting position", the user applies a distal pressure on the plunger rod 5 to move the first, second and third plugs 24, 21, 25. As shown on FIG. 15, the third plug 25 reaches a wider zone of the body 2 where it allows the medicine C to by-pass the third plug 25. The user can then proceed to a purge of the injection device 1 to ensure that no air will be injected by pursuing the displacement of the plunger rod 5 up to the first "pusher setting position" where the locker 7 comes in contact with the proximal end 4 of the body 2.

The user is then able to manually release the setting means 7 and to move said locker 7 in the proximal direction on as to immobilize it at a predetermined height of the plunger rod 5, in a second "locker setting position", by engaging a tooth (similar to the tooth 17 of FIGS. 1-4) of the locker 7 with the indent 33 of the plunger rod 5. The locker 7 is therefore immobilized on the plunger rod 5

After having immobilized the locker 7 to the second "locker setting position", the user insert the needle 36 in the injection site and proceeds to the injection by pushing distally on the plunger rod 5 until the locker 7 comes in contact with the proximal end 4 of the body 2, in a second "pusher setting position", shown on FIG. 16. In this case, all the medicine C is injected and, in the "pusher setting position", the first, second and third plugs 24, 21, 25 have reached the distal end of the body 2, in an end-of-use position, as shown on FIG. 16. The right dosage of medicine to be injected was predetermined by the distance between the first and the second "locker setting positions".

In another embodiment not shown, in the "pusher setting position", only a controlled dose of the medicine C has been injected, as wished by the user. If necessary, the user can then manually retract the locker 7 in the proximal direction, for instance until the locker 7 reaches the head 6 of the plunger rod 5 or any intermediate "locker setting position". In a complementary step, the user then continues to apply a distal pressure on the plunger rod 5 and completes the injection until the locker 7 comes in contact with the proximal end 4 of the body 2. The user can proceed the same way to other preset dose injection.

As shown particularly in this embodiment, the injection device 1 of the invention allows for several positions of setting means and of several steps of injection before the position of end-of-use is reached.

In the embodiments described previously, the plunger rod 5 has only one fixed stop 8 defining a single "locker (and pusher) locking position". In embodiments of the invention, not shown, the plunger rod has several fixed stops, each one defining a "locker (and pusher) locking position".

In other embodiments not shown, the plunger rod can also have several fixed stops arranged in different lines angularly located on the plunger rod. The fixed stop can be arranged differently on each line to define different setting lines, to each of which correspond different "locker and pusher setting positions". The injection device can be set to a predetermine line of "locker and pusher setting position when assembled by the angular positioning of the locker relative to the plunger rod. In other embodiment not shown, the injection device can also be set before use by the user by rotation of the locker relative to the pusher.

In the embodiments described previously, the locking and setting means prevent distal and proximal displacement of the locker either before reaching the "pusher locking position" or being manually triggered.

In other embodiments not shown, the displacement limitation can be limited to proximal displacement of the locker relative to the pusher.

In other embodiments not described, the locker can be designed in order to be able to be taken away from the pusher when the "pusher locking position" is reached. In this case, the setting means are at least partly formed by a separate button movable relative to the plunger rod and able to define at least one "locker and pusher setting position".

In another embodiment not shown, the locking means have a breakable part designed to be broken when the "pusher blocking position" is reached.

The container of the invention allows for safe completion of preparatory steps and further intermediate steps, such as purging of a syringe, reconstitution of a medicine such as contrast media or of a glue or any mixed product, or successive steps of injection or application of the product, without any risk of wasting some product or expelling incorrect doses of product, by inadvertent distal movement of the pusher. Indeed, the container of the invention:

thanks to the locking means, prevents the user from being able to manually displace the locker on the pusher before the pusher has reached a predetermined "pusher locking position", thanks to the unlocking means, automatically releases the locking means in the "pusher locking position", thanks to the setting means, prevents the inadvertent displacement of the locker in the "pusher locking position", enables the manual release of the setting means to allow the further displacement of the pusher.

Therefore, the container according to the invention can be used for completing at least two steps with the necessity to make a pause in the "pusher locking position" before starting the second step. This pause is imposed by the locking means which are automatically released when the "pusher locking position" is reached, but which cannot be manually released before said "pusher locking position" is reached. This pause is also imposed by the setting means which have to be manually released before enabling the locker to be moved, even though the locking means have been released in the "pusher locking position".

The invention claimed is:

1. A container (1) comprising at least:
a body (2) forming at least one cavity designed to contain at least one product (35),
a pusher (5) movable distally with respect to said body (2) between at least an initial position and an end-of-use position to expel at least part of said product (35) from said body (2),
a locker (7) located on said pusher (5) and forming an abutment so as to be able to abut against said body (2) in restricting the extent of distal movement of said pusher (5) with respect to said body (2), wherein, upon said pusher (5) moving distally with respect to said body between said initial position and said end-of-use position, said abutment abuts against said body to limit distal movement of said pusher (5) relative to said body (2) to a pusher locking position located between said initial position and said end-of-use position,
locking means (9, 9b, 8, 5, 4a, 11, 12, 15, 29, 29a, 30a) capable of, temporarily, locking said locker (7) on said pusher (5), at least in the proximal direction relative to said pusher (5), so as to define a locker locking position of said locker (7) on said pusher (5), said locker locking position establishing the position of said abutment relative to said pusher (5) so as to set said pusher locking position,
unlocking means (9, 9a 10, 29, 31, 13, 16, 17, 31) comprising at least one bearing surface (10; 13; 16; 31) designed for causing release of said locker (7) from said locker locking position, said unlocking means designed so that triggering thereof causes the release of said locking means so as to allow
i) said locker (7) to be displaced proximally relative to, and translatable along the length of, said pusher (5) and
ii) said pusher (5) to be moved distally past said pusher locking position toward said end-of-use position, wherein:
said locking means (9, 9b, 8, 5, 4a, 11, 12, 15, 29, 29a, 30a) are located partially on said pusher (5) and partially on said locker (7), and
with said pusher (5) being in said pusher locking position, and due to distal pressure exerted on said pusher (5), said at least one bearing surface (10; 13; 16; 31)

automatically releasing said locker (7) from said locker locking position on said pusher (5).

2. A container (1) according to claim 1, further comprising setting means (17, 33, 40, 5, 4a, 19, 20, 22, 43) designed to be:

capable of, temporarily, blocking said locker (7) on said pusher (5), at least in the proximal direction relative to said pusher (5), so as to define a locker setting position of said locker (7) on said pusher (5) proximally of locker locking position, wherein, with said locker (7) being in said locker setting position, and upon said pusher (5) moving distally with respect to said body (2) from said pusher locking position toward said end-of-use position, said abutment abuts against said body to limit distal movement of said pusher (5) relative to said body (2) to a pusher setting position, capable of being manually triggered so as to allow said locker (7) to be displaced proximally relative to said pusher (5) and said pusher (5) to be moved past said pusher setting position toward said end-of-use position.

3. A container (1) according to claim 2, wherein said locking means and/or setting means comprise at least one partially elastically deformable stop (9, 15, 19, 29) located on said locker (7) or pusher (5) and able to cooperate with said pusher (5) or locker (7) to define said pusher locking position and/or pusher setting position, said deformable stop (9, 15, 19, 29) being able to be deformed, in said pusher locking position and/or pusher setting position to allow at least the distal displacement of said pusher (5) relative to said body (2).

4. A container (1) according to claim 3, wherein deformable stop (19) can be manually deformed to release said setting means (19, 20).

5. A container (1) according to claim 3, wherein said locker (7) or pusher (5) comprises at least one flexible leg (9, 29) bent toward said pusher (5) or locker (7) with which it is engaged at least by friction, said flexible leg (9, 29) defining at least part of said locking means and/or setting means.

6. A container (1) according to claim 3, wherein said locker (7) comprises at least one longitudinal wall (15; 19) elastically deformable between an engaged position in which it is engaged at least by friction with said pusher (5) and a released position in which it releases said pusher (5), said longitudinal wall (15, 19) defining at least part of said locking means and/or setting means.

7. A container (1) according to claim 3, wherein said at least one bearing surface (10; 13; 16; 31) capable of, when said locker (7) is pressed against said body (2) in said pusher locking position, deforming said deformable stop (9, 15, 19, 29) to release said locking means.

8. A container (1) according to claim 7, wherein deformable stop (9, 15, 19, 29) comprises at least an inclined surface (14, 29), said bearing surface (10, 13, 16, 31) being also inclined in order to, when said locker (7) is pressed against said body (2) in said pusher locking position, said inclined surface (14, 29) and bearing surface (10, 13, 16, 31) cooperate with each other to deform said deformable stop (9, 15, 19, 29) and release said locking means.

9. A container (1) according to claim 3, wherein said deformable stop (9, 15, 19, 29) comprises at least one tooth (9b, 17, 11, 29a, 43) located either on said locker (7) or on said pusher (5), and at least one indent (8, 33, 12, 30a, 22) correspondingly located either on said pusher (5) or on said locker (7), said tooth (17) being engaged in said indent (33) before the release of said locking means and/or setting means.

10. A container (1) according to claim 2, wherein said locking means and/or setting means comprise at least one movable stop (11) located on said locker (7) or pusher (5) and able to cooperate with said pusher (5) or locker (7) to define said pusher locking position and/or pusher setting position, said movable stop (11) being able to be tangentially moved relative to said pusher (5), in said pusher locking position and/or pusher setting position to release at least the distal displacement of said pusher (5) relative to said body (2).

11. A container (1) according to claim 10, wherein said unlocking means comprise at least one bearing surface (10; 13; 16; 31) capable of, when said locker (7) is pressed against said body (2) in said pusher locking position, moving said movable stop (11) to release said locking means.

12. A container (1) according to claim 11, wherein said movable stop (11) comprises at least an inclined surface (14, 29), said bearing surface (10, 13, 16, 31) being also inclined in order to, when said locker (7) is pressed against said body (2) in said pusher blocking position, said inclined surface (14, 29) and bearing surface (10, 13, 16, 31) cooperate with each other to move said movable stop (11) and release said locking means.

13. A container (1) according to claim 10, wherein said movable stop (11) comprises at least one tooth (9b, 17, 11, 29a, 43) located either on said locker (7) or on said pusher (5), and at least one indent (8, 33, 12, 30a, 22) correspondingly located either on said pusher (5) or on said locker (7), said tooth (17) being engaged in said indent (33) before the release of said locking means and/or setting means.

14. A container (1) according to claim 2, wherein said locking means and/or setting means comprise at least one breakable stop located on said locker (7) or pusher (5) and able to cooperate with said pusher (5) or locker (7) to define said pusher locking position and/or pusher setting position, said breakable stop being able to be broken by the action of said unlocking means and/or manually, in said pusher locking position and/or pusher setting position to release at least the distal displacement of said pusher (5) relative to said body (2).

15. A container (1) according to claim 14, wherein said unlocking means comprise at least one bearing surface (10; 13; 16; 31) capable of, when said locker (7) is pressed against said body (2) in said pusher locking position, breaking said breakable stop to release said locking means.

16. A container (1) according to claim 15, wherein said breakable stop comprises at least an inclined surface (14, 29), said bearing surface (10, 13, 16, 31) being also inclined in order to, when said locker (7) is pressed against said body (2) in said pusher locking position, said inclined surface (14, 29) and bearing surface (10, 13, 16, 31) cooperate with each other to break said breakable stop and release said locking means.

17. A container (1) according to claim 14, wherein said breakable stop comprises at least one tooth (9b, 17, 11, 29a, 43) located either on said locker (7) or on said pusher (5), and at least one indent (8, 33, 12, 30a, 22) correspondingly located either on said pusher (5) or on said locker (7), said tooth (17) being engaged in said indent (33) before the release of said locking means and/or setting means.

18. A container (1) according to claim 2, wherein said locker (7) defines a recess (23, 32) in which at least a part of the cross section of said pusher (5) is housed.

19. A container (1) according to claim 18, wherein said locker (7) is being provided in its recess (32) with at least one radial tooth (9b, 17, 11, 29a, 43) designed to engage with an indent (8, 33, 12, 30a, 22) on said pusher (5), said radial tooth (9b, 17, 11) and indent (8, 33, 12) defining at least in part said setting means and/or said locking means.

20. A container (1) according to claim 19, wherein, at least part of the cross section of said pusher (5) has a H shape, said recess (32) of said locker (7) is opened and has a C shape complementary to a first side of said H shape engaged in said C shape, the second side of said H shape receiving a flexible leg (40) extending from said locker (7) in order to press said C shape against said H shape of said pusher (5) and block said locker (7) on said pusher (5).

21. A container (1) according to claim 19, wherein said locker (7) and said pusher (5) are respectively being provided with two sets of radial teeth (17) and indents (33), one setting set for the setting means and one locking set for the locking means, the setting and locking sets being located at a different distance from said pusher (5) axis to allow:
   to keep the engagement of both said locking and setting sets before reaching the pusher blocking position, and
   to keep the engagement of said setting set after the release in said pusher blocking position of said locking set up to the manual release of said setting means.

22. A container (1) according to claim 18, wherein said locker (7) is being provided with at least one flexible radial tab (9) designed to engage with a spur (8) on said pusher (5) and to define at least in part said locking means, and in that said radial tab (9) is continued at its distal end by a deactivating tab (9a) designed to engage with said body (2) to disengage said radial tab (9) from said spur (8) to unlock said locking means, said deactivating tab (9a) defining at least part of said unlocking means.

23. A container (1) according to claim 2, wherein said locker (7) is made of at least two parts, one part comprising at least part of the locking means, the other part comprising at least part of the setting means.

24. A non therapeutic method for using a container (1) in particular for the preparation of a product (35), said method comprising at least the following successive steps:
   a) a container (1) according to claim 2 is provided, said container (1) being in the initial position with said locker (7) in said locker locking position on said pusher (5),
   b) said pusher (5) is pushed distally relative to said body (2) up to the pusher locking position and up to the release of said locking means,
   c) said setting means are then manually released,
   d) said locker (7) is displaced proximally on to said pusher (5) up to said locker setting position,
   e) said pusher (5) is moved distally relative to said body (2) up to said pusher setting position.

25. A method according to claim 24, wherein said locking means (9, 9b, 8, 5, 4a, 11, 12, 15, 29, 29a, 30a) define a said locker locking position which corresponds to a locker setting position in order to, when the locking means are automatically released in said pusher setting/locking position, have the setting means prevent the pusher (5) from being moved passed said pusher setting/locking position until manual release of said setting means.

26. A method according to claim 25, wherein after the triggering of said unlocking means and release of said locking means, said locker (7) is able to be taken away from said body (2).

27. A container (1) according to claim 1, wherein said locker (7) is mobile in rotation with respect to said pusher (5).

28. A container (1) according to claim 1, wherein the unlocking means are designed to prevent their manual triggering before reaching said pusher locking position.

29. A container (1) according to claim 28, wherein at least part of the unlocking means are embedded in the locker (7).

30. A container (1) according to claim 1, wherein said locker (7) has a symmetry of revolution about the longitudinal axis of said pusher (5).

31. A device (1) comprising a container (1) according to claim 1, in which said body (2) is a barrel, said pusher (5) is a plunger rod and said locker is a button (7) movable at least in translation along said plunger rod (5).

32. A device (1) according to claim 31, further comprising at least a first plug (24), a second plug (21) and a third plug (25), all contained within said barrel (2), said first plug (24) being in a more proximal position than said second plug (21) and designed to be linked to said pusher (5), said third plug (25) being in a more distal position than said second plug (21), said first, second and third plugs (24, 21, 25) being movable in translation at least between:
   an initial position, in which said first plug (24) and said second plug (21) define a first chamber (26) containing a substance A, and said second plug (21) and said third plug (25) define a second chamber (27) containing a substance B,
   a by-pass position, in which said first, second and third plugs (24, 21, 25) are located distally forward from the initial position, said second plug (21) being located in a transfer zone (28) provided for this purpose within said body (2) to allow the transfer of substance A from said first chamber (26) to said second chamber (27),
   a mixing position corresponding to said pusher locking position and in which all of substance A has reached, via the transfer zone (28), all of substance B in said second chamber (27), said first plug (24) having moved in the distal direction until it has made contact with said second plug (21), the third plug (25) having not moved significantly, the distance between said locking means (9) and said unlocking means (10) in the by-pass position being the same as the distance traveled by said first plug (24) from said by-pass position to said mixing position,
   an open position in which said first, second and third plugs have been distally moved forward from said mixing position, said third plug being located in a wider zone provided to allow said substances A and B to by-pass said third plug.

33. A device (1) according to claim 32, wherein, after said open position, said first, second and third plugs (24, 21, 25) are movable to a pusher setting position corresponding to said pusher setting position and in which said first and second plug (24, 21) have moved toward said third plug (25) compared to the open position, the distance between said setting means (9) and said body (2) in the open position being the same as the distance traveled by said first and second plug (24, 21) from said open position to said pusher setting position.

34. A device (1) according to claim 32, wherein, after said open position, said first, second and third plugs (24, 21, 25) are movable to an end of use position in which, the first, second and third plug (24, 21, 25) have reached the distal end of said body (2).

* * * * *